(12) United States Patent
Kruit (10) Patent No.: US 9,449,789 B2
(45) Date of Patent: Sep. 20, 2016

(54) APPARATUS AND METHOD FOR INSPECTING A SURFACE OF A SAMPLE

(71) Applicant: Technische Universiteit Delft, Delft (NL)

(72) Inventor: Pieter Kruit, Delft (NL)

(73) Assignee: TECHNISCHE UNIVERSITEIT DELFT, Delft (NL)

( * ) Notice: Subject to any disclaimer, the term of this patent is extended or adjusted under 35 U.S.C. 154(b) by 0 days.

(21) Appl. No.: 14/437,738

(22) PCT Filed: Oct. 24, 2013

(86) PCT No.: PCT/NL2013/050746
§ 371 (c)(1),
(2) Date: Apr. 22, 2015

(87) PCT Pub. No.: WO2014/065663
PCT Pub. Date: May 1, 2014

(65) Prior Publication Data
US 2015/0270095 A1 Sep. 24, 2015

(30) Foreign Application Priority Data
Oct. 25, 2012 (NL) ...................................... 2009696

(51) Int. Cl.
*H01J 37/28* (2006.01)
*H01J 37/244* (2006.01)
(Continued)

(52) U.S. Cl.
CPC ........... *H01J 37/28* (2013.01); *G01N 23/2251* (2013.01); *H01J 37/244* (2013.01);
(Continued)

(58) Field of Classification Search
CPC .......... H01J 37/28; H01J 37/05; H01J 37/10; H01J 37/1474; H01J 37/3177; H01J 37/04; H01J 37/045; H01J 37/141; H01J 37/147; H01J 37/256; H01J 37/26; G01N 23/2251; B82Y 10/00; B82Y 40/00
USPC ................ 250/306, 305, 307, 310, 311, 309, 250/396 R, 398, 395, 396 ML, 492.1, 49, 250/2.2, 492.22, 492.23
See application file for complete search history.

(56) References Cited

U.S. PATENT DOCUMENTS

| 4,823,006 A | 4/1989 | Danilatos et al. |
| 7,732,762 B2 * | 6/2010 | Nijkerk ............. G01N 23/2251 250/306 |

(Continued)

FOREIGN PATENT DOCUMENTS

WO 2007028596 3/2007

*Primary Examiner* — David A Vanore
(74) *Attorney, Agent, or Firm* — Dann, Dorfman, Herrell and Skillman; Stephen Eland (57) ABSTRACT

The invention relates to an apparatus and method for inspecting a sample. The apparatus comprises a generator for generating an array of primary charged particle beams (33), and a charged particle optical system with an optical axis (38). The optical system comprises a first lens system (37, 310) for focusing all primary beams (33) into a first array of spots in an intermediate plane, and a second lens system (313, 314) for focusing all primary beams (33) into a second array of spots on the sample surface (315). The apparatus comprises a position sensitive backscattered charged particle detector (311) positioned at or near the intermediate plane. The second lens system comprises an electromagnetic or electrostatic lens which is common for all charged particle beams. Preferably the second lens system comprises a magnetic lens for rotating the array of primary beams (33) around the optical axis (38) to position the second array of charged particle spots with respect to the first array at an angle.

27 Claims, 5 Drawing Sheets

(51) Int. Cl.
  *G01N 23/225* (2006.01)
  *H01J 37/317* (2006.01)
(52) U.S. Cl.
  CPC ....... *H01J37/3177* (2013.01); *G01N 2223/33* (2013.01); *G01N 2223/3307* (2013.01); *G01N 2223/413* (2013.01); *G01N 2223/418* (2013.01); *H01J 2237/2446* (2013.01)

(56) References Cited

U.S. PATENT DOCUMENTS

| | | | | |
|---|---|---|---|---|
| 7,829,853 B2 * | 11/2010 | Watanabe | ........ | G01N 23/2251 250/306 |
| 7,947,951 B2 * | 5/2011 | Khursheed | ........ | H01J 37/05 250/305 |
| 8,039,813 B2 * | 10/2011 | Casares | ........ | H01J 37/045 250/306 |
| 8,350,214 B2 * | 1/2013 | Otaki | ........ | B82Y 10/00 250/310 |
| 9,035,249 B1 * | 5/2015 | Frosien | ........ | H01J 37/05 250/310 |
| 9,263,233 B2 * | 2/2016 | Zeidler | ........ | H01J 37/28 |
| 9,349,571 B2 * | 5/2016 | Kemen | ........ | H01J 37/265 |
| 2005/0214958 A1 | 9/2005 | Nakasuji et al. | | |
| 2010/0133433 A1 * | 6/2010 | Tanimoto | ........ | H01J 37/244 250/310 |
| 2010/0320382 A1 * | 12/2010 | Almogy | ........ | H01J 37/05 250/307 |
| 2015/0144787 A1 * | 5/2015 | Benner | ........ | H01J 37/26 250/307 |
| 2015/0170876 A1 * | 6/2015 | Janssen | ........ | H01J 37/28 250/307 |

* cited by examiner

APPARATUS AND METHOD FOR INSPECTING A SURFACE OF A SAMPLE

BACKGROUND

The invention relates to an apparatus and a method for inspecting a surface of a sample. In particular the invention relates to an apparatus for inspecting a sample surface using a plurality of charged particle beams, such as a multi-beam scanning electron microscope. The invention may be applied to charged particles of any type, such as electrons, positrons, ions and others.

The invention relates to an apparatus for detecting backscattered charged particles, such as electrons. These backscattered charged particles have almost the same energy as the primary charged particles. It is usually assumed that the charged particles lose up to a few hundred electron volts in the sample before coming out again. The angular distribution of the backscattered charged particles is much larger than the angular distribution of the primary charged particle beams. The backscattered charged particles that travel close to the axis of corresponding primary charged particle beam will travel back through the charged particle optical system along paths that closely resemble the primary charged particles and they will focus in about the same planes as the primary charged particle beams.

Such an apparatus is for example disclosed in U.S. Pat. No. 7,732,762. This US patent discloses an electron microscope comprising an electron emitter which, in use, emits a plurality of primary electron beams which are directed towards a surface of a specimen. The apparatus comprises a first lens system for focusing the electron beams into a first array of separated spots in an intermediate plane between the electron emitter and the specimen surface. The apparatus further comprises a second lens system for directing the primary electron beams from the intermediate plane towards the specimen surface and for focusing all primary electron beams into a second array of individual spots on the specimen surface. In particular the second lens system comprises a cascade of lenses, more in particular a microlens array which comprises an individual microlens for each individual electron beam.

At the intermediate plane, a thin sheet-like plate comprising fluorescent material is disposed. The thin sheet comprises apertures, so that the primary electron beams are allowed to pass. The plate collects the back-scattered electrons and converts the collected electrons into photons. The photons are at least partially directed to an array of photo detectors by means of an optical lens system.

A disadvantage of this system is that the distance between the individual spots on the specimen surface is relatively large due to the use of one objective microlens per electron beam. Consequently the known system is less suitable for inspecting small samples.

It is an object of the present invention to provide a multi charged particle beam apparatus for inspecting a sample surface which provides a new detection arrangement for detecting the back-scattered electrons.

SUMMARY OF THE INVENTION

According to a first aspect, the invention provides an apparatus for inspecting a surface of a sample, wherein the apparatus comprises a multi beam charged particle generator for generating an array of primary charged particle beams, and a charged particle optical system with an optical axis comprising:

a first lens system for focusing the primary charged particle beams into a first array of separated spots in an intermediate plane, and a second lens system for directing the primary charged particle beams from the intermediate plane towards the sample surface and which comprises an electromagnetic or electrostatic objective lens which is common for at least the primary charged particle beams for focusing all primary charged particle beams into a second array of individual spots on the sample surface, wherein the apparatus comprises a position sensitive backscatter charged particle detector positioned in or near the intermediate plane, wherein said detector comprises one or more through openings for passing said primary charged particle beams there through, and wherein said second lens system is arranged for projecting backscattered charged particles from the second array of individual spots on the sample surface into an array of backscattered charged particle spots on the detector Using a single objective lens which is common for at least the primary charged particle beams, the individual spots on the sample surface can be arranged much closer to each other due to the use of the common lens for focusing all primary charged particle beams into the second array of individual spots on the sample surface. This makes the multi-beam apparatus of the invention more suitable for inspecting smaller samples, for example having a surface area of 1 mm$^2$ or even smaller.

It is noted that in the context of this application, a surface of a sample encompasses the top layer of the sample including material just below the boundary plane of the sample.

It is further noted that in the context of this application, the one or more through openings for passing said primary charged particle beams there through, may comprise one or more holes in the detector, and may also comprise an opening adjacent to the detector.

Preferably the intermediate plane where the primary beams are smallest is close to the plane in which the backscattered charged particles are also focused, at which plane the detector is preferably situated.

In an embodiment the one or more through openings comprises an array of holes wherein each hole of the array of holes is arranged for passing one of said array of primary charged particle beams there through. In an embodiment, the diameter of the holes of the array of holes is substantially smaller than the pitch between the holes. Since the detector is arranged at least substantially in or near the intermediate plane where the primary charged particle beams are focused, the primary charged particle beams pass through sufficiently small holes in the detector so that there is enough surface area in the detector to allow efficient detection.

However, arranging the individual spots much closer to each other on the sample surface according to the invention makes it more difficult to separate and distinguish backscattered charged particles from different spots on the sample surface. For example as shown in the apparatus as disclosed in U.S. Pat. No. 7,732,762, the backscattered electrons are imaged at or around the position of the focused primary beams at the plate of fluorescent material. In this apparatus, a part of the backscattered electrons passes through the apertures in the plate of fluorescent material and are not detected. In the apparatus of the prior art, only the backscattered electrons which are not focused in the same spots as the primary beams and which form blurred spots at the plate of fluorescent material can be detected.

On the one hand this further problem can be solved by an embodiment, wherein the second lens system is arranged for imaging the first array of separated spots from said intermediate plane onto the sample surface with a magnification in a range from 0.01 to 0.2. Thus the distance between adjacent spots at the detector is up to a 100 times larger then adjacent spots on the sample surface.

On the other hand this further problem can be solved in an embodiment of the invention, wherein the second lens system comprises one or more magnetic lenses which are arranged for rotating the array of primary charged particle beams around the optical axis on their way from said intermediate plane towards the sample, to position the second array with respect to the first array at an angle larger than 0 degrees and preferably smaller than 180 degrees around the optical axis. In an embodiment, the one or more magnetic lenses are arranged for rotating the array of backscattered charged particle spots with respect to the first array at an angle larger than 0 degrees and preferably smaller than 360 degrees around the optical axis. It is noted that is also possible to combine the two later embodiments.

By using a magnetic lens, the position of the second array is rotated with respect to the first array with an angle between 0 and 180 degrees. The backscattered charged particles, which preferably also pass through the same magnetic lens, are also rotated with respect to the second array with substantially the same angle between 0 and 180 degrees. It is noted that the rotation of the backscattered charged particles is in the same rotation direction as the rotation of the primary charged particle beams. The array of spots of the backscattered charged particles on the position sensitive detector at the intermediate plane is thus rotated with respect to the first array at an angle larger than 0 degrees and smaller than 360 degrees around the optical axis. This rotation provides a spatial separation between the array of spots of the backscattered charged particles with respect to the first array of separated spots of the primary beams at or near the intermediate plane, which allows to arrange the array of spots of the backscattered charged particles at a position in which they at least substantially deviate from the position of the first array. Thus by carefully selecting the rotation, the detection of the backscattered charged particles at or near the intermediate plane, at least substantially does not interfere with the passing of the primary charged particle beams. In the apparatus according to the invention, also the backscattered charged particles which are at least substantially focused in the intermediate plane can be detected.

Contrarily to the apparatus according to U.S. Pat. No. 7,732,762, the second lens system and/or the position of the detector in the apparatus of the invention can now be arranged in order to at least substantially reduce the blur of the spots of backscattered charged particles, or to focus the backscattered charged particles on small spots, which enhances the resolution of the detection arrangement of the invention.

In an embodiment, the second lens system is arranged for projecting the backscatter charged particles from the individual spots on the sample surface through a common cross-over of the backscattered charged particles to substantially individual spots on the position sensitive backscatter charged particle detector. In an embodiment, an aperture is arranged in or near the plane comprising the common cross-over of the backscattered charged particles. Such a backscatter beam limiting aperture between the sample and the detector limits the acceptance angle of the backscattered charged particles, and is used to influence the contrast in the image of backscattered particles on the detector. The aperture can also be used to control and limit the size of the spots of backscattered particles on the detector. In an embodiment, said aperture comprises open areas to allow passage of certain angular directions of the backscattered charged particles, while blocking other angular directions.

In an embodiment, the one or more magnetic lenses are arranged for rotating the array of backscattered charged particle spots with respect to the first array at an angle of substantially 180 degrees around the optical axis. In an embodiment, the detector comprises one through opening for passing said primary charged particle beams there through. Preferably this through opening is arranged adjacent to the detector or to the sensitive surface of the detector.

In an embodiment, the position sensitive backscatter charged particle detector contains more than one pixel per backscatter charged particle beam. When using a position sensitive backscatter charged particle detector having many more pixels than backscatter spots, the backscatter signal is obtained by reading out the pixels of the detector. There is no need to determine in advance the location in the detector plane where the backscatter spots are going to end up.

In an embodiment, the position sensitive backscatter charged particle detector is a CCD camera, a CMOS camera, an array of avalanche photo diodes, photo multipliers or PN junction semiconductor detector which gets signal from backscatter charged particles directly.

In an embodiment, the position sensitive backscatter charged particle detector comprises a fluorescent screen arranged at least substantially in or near said intermediate plane and an optical arrangement for conveying photons from the fluorescent screen to a CCD camera, a CMOS camera, an array of avalanche photo diodes or photo multipliers.

In an embodiment, the CCD camera, CMOS camera, array of avalanche photo diodes or photo multipliers is positioned such that the array of detector pixels coincides with the array of images of the individual backscatter beams.

In an embodiment, the pitch between the spots in the second array of separated spots on the sample surface is between 0.3 and 30 micrometers.

In an embodiment, the second lens system comprises magnetic and/or electrostatic charged particle deflectors for scanning the primary charged particle over the sample. In an embodiment, the magnetic and/or electrostatic charged particle deflectors are arranged and/or controllable for obtaining a substantially stationary positioning of the array of backscattered charged particle spots on the detector during scanning. A magnetic deflector deflects charged particles on their way towards the sample in the opposite direction as the charged particles moving from the sample to the detector. The latter causes a movement of the backscattered electron spots on the detector while scanning the primary beam. An electrostatic deflector, on the contrary, deflects beams of charged particle into a direction which is independent on the direction of the particles. Thus, employing an electrostatic deflector would seem to ensure no movement of the spots on the detector. However, the rotation of the image by the magnetic lens may still leave a movement. A double system of both magnetic and electrostatic deflectors gives sufficient adjustable parameters that the setting can be chosen during operation in order to ensure stable spot position on the detector during scanning.

In an embodiment, the second lens system is arranged for projecting the primary charged particle beams through a common cross-over, and wherein the apparatus comprises a position sensitive secondary electron detector positioned at least substantially in or near a plane comprising said common cross-over. As discussed in more detail in the Dutch Patent Application 2009053, this embodiment provides a detection system in which the secondary electrons are detectable. This embodiment utilizes the energy difference between the secondary electrons and the primary charged particles, for example in a SEM the energy of the primary electrons is usually from 1 keV to 30 keV and the energy of secondary electrons is usually from 0 eV to 50 eV. The result of this energy difference is that the second lens system performs differently for primary charged particles than for secondary electrons. On the one hand, the second lens system is arranged for focusing all primary charged particle beams into an array of individual spots on the sample surface. On the other hand, the same lens system is used for directing the secondary electron beams towards the plane of the common cross-over. Since the secondary electrons have an energy which is much less than the energy of the primary charged particles, the lens system is arranged to spread the secondary electrons over an area which essentially surrounds the common cross-over. Thus, in or near a plane comprising said common cross-over, most of the secondary electron beams are spatially separated from the primary charged particle beams which are all concentrated in the common cross-over. It is noted that also the backscattered charged particles are at least substantially concentrated in the common cross-over, and thus are spatially separated from the secondary electron beams.

By positioning a position sensitive secondary electron detector at least substantially in or near a plane comprising said common cross-over, preferably adjacent to and/or surrounding the common cross-over, most of the secondary electron beams can be detected without any interference to the primary charged particle beams or the backscattered charged particles.

Accordingly, in an apparatus according to the invention, and in particular according to this embodiment, the backscattered charged particles are detectable using detectors arranged in the charged optical column of the apparatus. In addition, both the backscattered charged particles and the secondary electrons can be detected separately and substantially simultaneous.

According to a second aspect, the invention provides a method for inspecting a surface of a sample comprising the steps of:

generating an array of primary charged particle beams using a multi beam charged particle generator;

focusing the primary charged particle beams into a first array of separated spots in an intermediate plane, using a first lens system;

directing the primary charged particle beams from the intermediate plane towards the sample surface using a second lens system and focusing all primary charged particle beams into a second array of individual spots on the sample surface using an electromagnetic or electrostatic objective lens which is common for at least the primary charged particle beams;

projecting backscattered charged particles from the second array of individual spots on the sample surface into an array of backscattered charged particle spots on the intermediate plane using said second lens system; and detecting said backscattered charged particles using a position sensitive backscatter charged particle detector positioned in or near the intermediate plane, wherein said detector comprises one or more through openings for passing said primary charged particle beams there through.

In an embodiment, the second lens system comprises one or more magnetic lenses which are arranged to rotate the array of primary charged particle beams around the optical axis on their way from said intermediate plane towards the sample, and to position the second array with respect to the first array at an angle larger than 0 degrees and preferably smaller than 180 degrees around the optical axis. In an embodiment, the one or more magnetic lenses are arranged to rotate the array of backscattered charged particle spots with respect to the first array at an angle larger than 0 degrees and preferably smaller than 360 degrees around the optical axis.

In an embodiment, the one or more magnetic lenses are arranged to rotate the array of backscattered charged particle spots with respect to the first array at an angle of substantially 180 degrees around the optical axis. In an embodiment, the detector comprises one through opening for passing said primary charged particle beams there through.

In an embodiment, the second lens system comprises magnetic and/or electrostatic charged particle deflectors to scan the primary charged particle over the sample. In an embodiment, the magnetic and/or electrostatic charged particle deflectors are arranged and/or controllable to obtain a substantially stationary positioning of the array of backscattered charged particle spots on the detector during scanning.

In an embodiment, the sample surface is moved at constant speed in a first direction while the primary charged particle beams are scanned repeatedly in a second direction at least substantially perpendicular to the first direction. This provides a new way of studying samples with a scanning charged particle beam microscope: off-line microscopy wherein a full sample surface, for example over an area of one square millimeter, is scanned and imaged at nanometer resolution after which the full sample surface is available to the specialist, for example a biologist, for studying and/or inspecting the image on a computer, instead of behind the microscope.

According to a third aspect, the invention provides an apparatus for inspecting a surface of a sample, wherein the apparatus comprises a multi beam charged particle generator for generating an array of primary charged particle beams, and a charged particle optical system with an optical axis comprising:

a first lens system for focusing the primary charged particle beams into a first array of separated spots in an intermediate plane, and a second lens system for directing the primary charged particle beams from the intermediate plane towards the sample surface and for focusing all primary charged particle beams into a second array of individual spots on the sample surface, wherein the apparatus comprises a position sensitive backscatter charged particle detector positioned at least substantially in or near the intermediate plane, and in that the second lens system comprises an electromagnetic lens which is common for at least the primary charged particle beams and which is arranged for rotating the array of primary charged particle beams around the optical axis to position the second array with respect to the first array at an angle larger than 0 degrees and smaller than 180 degrees around the optical axis.

In an embodiment, the second lens system comprises a single objective lens. In an embodiment, this single objective lens is the electromagnetic lens which is arranged for rotating the array of primary charged particles beams around the optical axis. In an alternative embodiment, the single objective lens is an additional lens between the electromagnetic lens and the sample. In this alternative embodiment, the single objective lens comprises a electromagnetic lens or an electrostatic lens.

The various aspects and features described and shown in the specification can be applied, individually, wherever possible. These individual aspects, in particular the aspects and features described in the attached dependent claims, can be made subject of divisional patent applications.

BRIEF DESCRIPTION OF THE DRAWINGS

The invention will be elucidated on the basis of an exemplary embodiment shown in the attached drawings, in which.

DETAILED DESCRIPTION OF THE INVENTION

Figure 1:
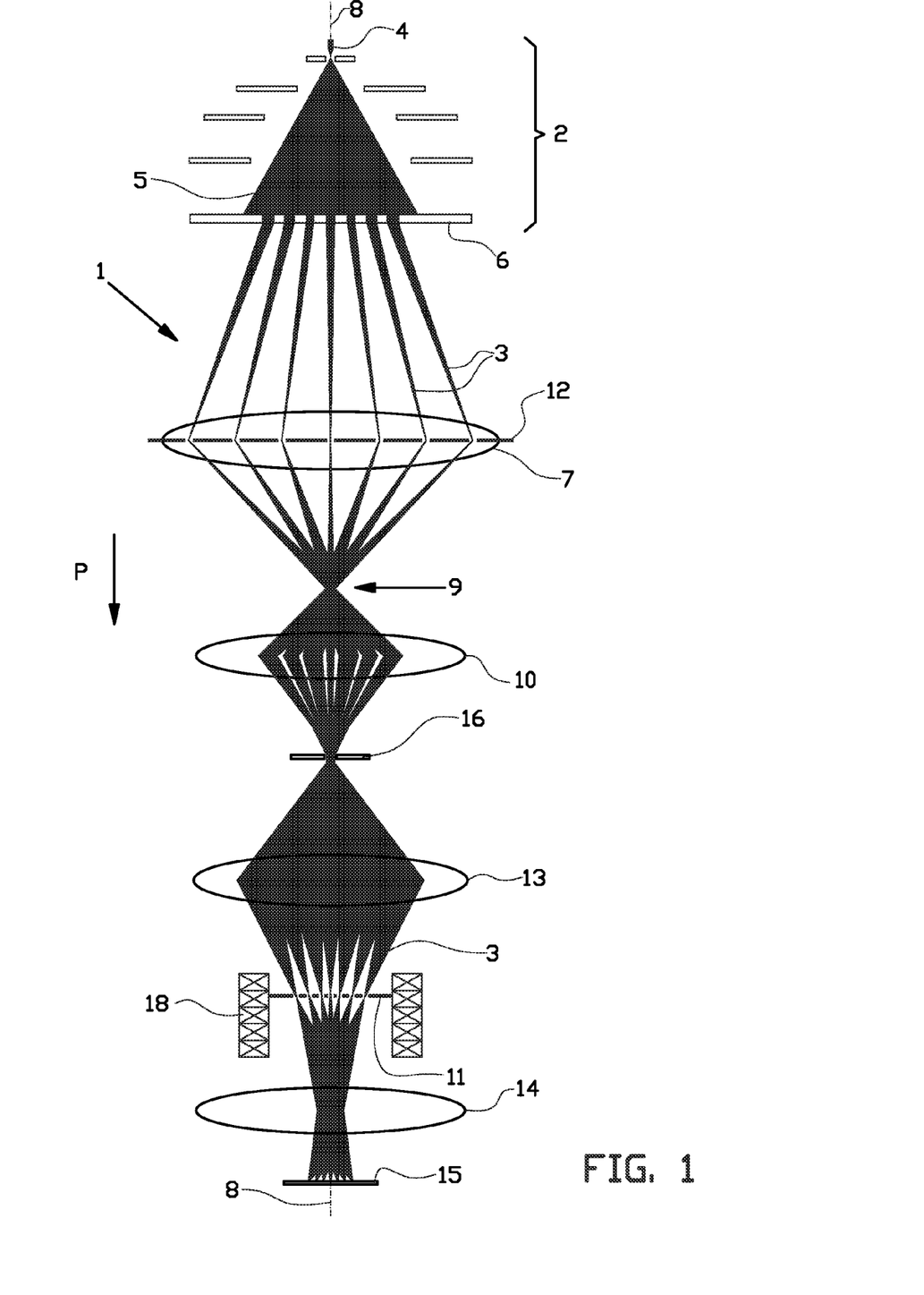
FIG. 1 shows an example of a Multi-Beam Scanning Electron Microscope (MBSEM) according to the invention.

FIG. 1 shows an example of a Multi-Beam Scanning Electron Microscope (MBSEM) of the invention.

The MBSEM 1 comprises a multi beam charged particle generator 2 for generating an array of primary charged particle beams 3, in this case an array of primary electron beams 3. The multi beam electron generator 2 comprises at least one electron source 4 for generating a diverging electron beam 5. The diverging electron beam 5 is split into an array of focused primary electron beams 3 by an aperture lens array 6. The primary electron beams 3 are subsequently directed towards a sample 15, as schematically indicated by the arrow P.

The multiple images of the source 4 are positioned on the object principle plane of an accelerator lens 7. The accelerator lens 7 directs the primary electron beams 3 towards the optical axis 8 and creates a first common cross-over 9 of all the primary electron beams 3.

The first common cross-over 9 is imaged by the magnetic condenser lens 10 onto a variable aperture 16 that acts as a current limiting aperture. At the variable aperture 16 a second common cross-over of all the primary electron beams 3 is created.

The MBSEM comprises a lens system 13, 14 for directing the primary charged particle beams from the common cross-over at the variable aperture 16 towards the sample surface 15 and for focusing all primary charged particle beams 3 into an array of individual spots on the sample surface 15. The lens system comprises an intermediate magnetic lens 13 for imaging the variable aperture 16 onto a coma free plane of the objective lens 14, which objective lens 14 creates an array of focused primary electron beams on the sample surface 15.

In addition the MBSEM is provided with scan coils 18 for scanning the array of focused primary electron beams over the sample surface 15.

In the MBSEM as shown in FIG. 1, there are at least two alternative positions which are suitable for detecting the backscattered charged particles:

A first position can be found between the intermediate magnetic lens 13 and the objective lens 14. In this case the intermediate magnetic lens 13 is at least part of the first lens system which focuses the primary electron beams 3 into a first array of separated spots in an intermediate plane where a position sensitive backscatter charged particle detector 11 is arranged, as shown in FIG. 1. The objective lens 14 is at least part of the second lens system for directing the primary electron beams 3 from the detector 11 plane towards the surface of the sample 15, and for focusing all primary charged particle beams 3 into a second array of individual spots. The objective lens 14 comprises an electromagnetic lens which is common for the primary electron beams 3 and is arranged for rotating the array of primary electron beams 3 around the optical axis 8 to position the second array on the target 15 with respect to the first array at the detector 11 plane at an angle larger than 0 degrees and smaller than 180 degrees around the optical axis 8, as will be explained in more detail in the discussion of FIGS. 4 and 5 below.

A second position can be found between the aperture lens array 6 and the magnetic condenser lens 10. In this case the aperture lens array 6 is at least part of the first lens system which focuses the primary electron beams 3 into a first array of separated spots in an intermediate plane where a position sensitive backscatter charged particle detector 12 is arranged, as shown in FIG. 1. The magnetic condenser lens 10 is at least part of the second lens system for directing the primary electron beams 3 from the detector 12 plane towards the surface of the sample 15, and for focusing all primary charged particle beams 3 into a second array of individual spots. The second lens system comprises an electromagnetic lens which is common for the primary electron beams 3. One or more of the magnetic condenser lens 10, the intermediate magnetic lens 13 and the objective lens 14 comprises the electromagnetic lens, which is arranged for rotating the array of primary electron beams 3 around the optical axis 8 to position the second array on the target 15 with respect to the first array at the detector 12 plane at an angle larger than 0 degrees and smaller than 180 degrees around the optical axis 8, as will be explained in more detail in the discussion of FIGS. 4 and 5 below.

It is noted that in order to detect the backscattered electrons, a detector is either arranged at the position of the first detector 11, or at the position of the second detector 12. The backscattered electron detector 11, 12 is arranged to acquire the individual backscatter electron image of each single primary electron beam spot on the sample surface 15. This means, that when the sample surface 15 is scanned in this MBSEM 1, multiple images can be acquired at the same time in one single scan period.

Figure 2:
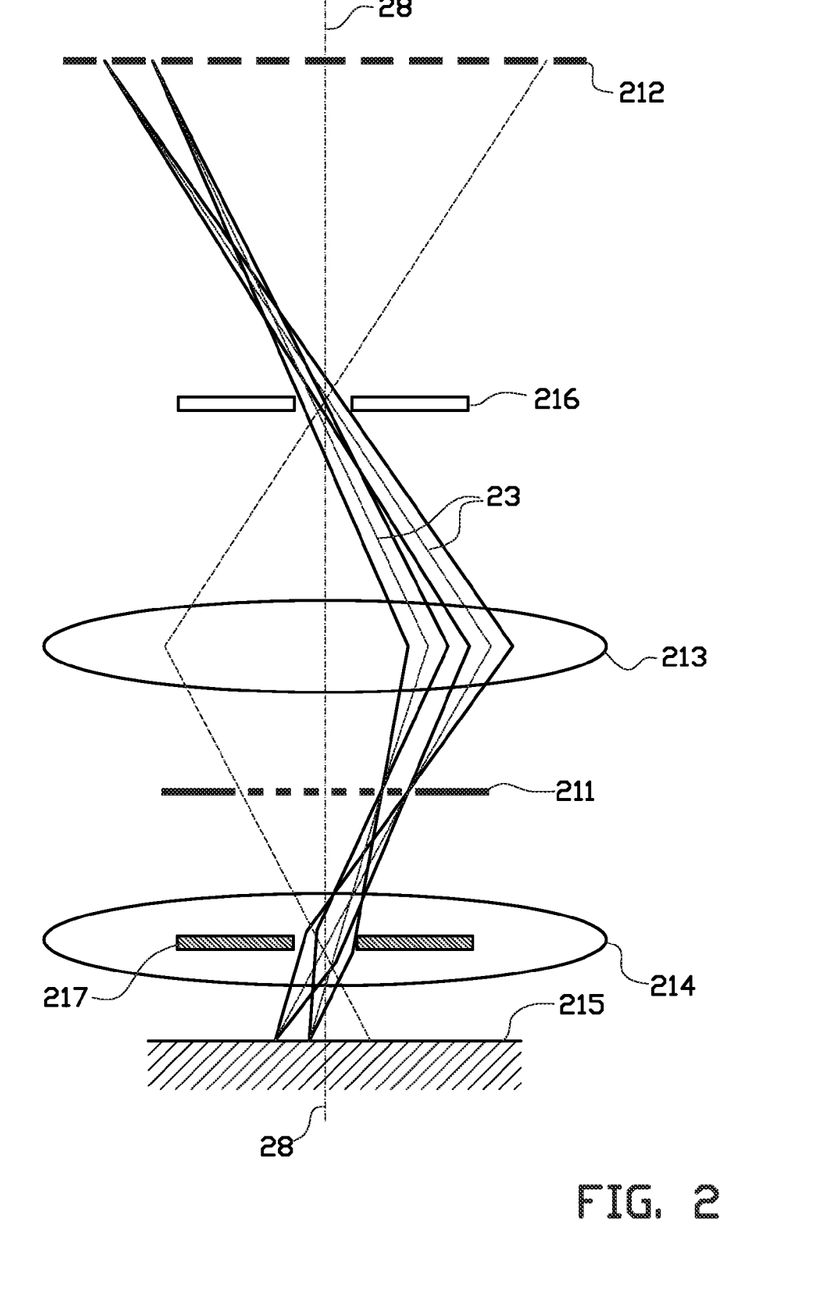
FIG. 2 shows part of the beam path of a second example of a MBSEM according to the invention.

FIG. 2 shown a schematic and simplified representation of the same set-up of FIG. 1, in particular the example as shown in FIG. 2 only comprises one common cross-over at the position of the variable aperture 216, in stead of the two common cross-over in FIG. 1. When using only one common cross-over, the magnetic condenser lens 10 as shown in FIG. 1 can be omitted.

Again, in the setup as shown in FIG. 2, there are two positions which are suitable for detecting the backscattered charged particles:

A first position can be found between the intermediate magnetic lens 213 and the objective lens 214. In this case the intermediate magnetic lens 213 is at least part of the first lens system which focuses the primary electron beams 23 into a first array of separated spots in an intermediate plane where a position sensitive backscatter electron detector 211 is arranged, as shown in FIG. 2. The objective lens 214 is at least part of the second lens system for directing the primary electron beams 23 from the detector 211 plane towards the surface of the sample 215, and for focusing all primary charged particle beams 23 into a second array of individual spots. The objective lens 214 comprises an electromagnetic lens which is common for the primary electron beams 23 and is arranged for rotating the array of primary electron beams 23 around the optical axis 28 to position the second array on the target 215 with respect to the first array at the detector 211 plane at an angle larger than 0 degrees and smaller than 180 degrees around the optical axis 28, as will be explained in more detail in the discussion of FIGS. 4 and 5 below.

It is noted that in the objective lens 214, a variable aperture 217 is arranged as a backscatter beam limiting aperture between the sample 215 and the detector 211. The backscatter beam limiting aperture 217 limits the acceptance angle of the backscattered electrons, and is used to influence the contrast in the image of backscattered particles on the detector 211. The aperture 217 can also be used to control and limit the size of the spots of backscattered particles on the detector 211.

Alternatively, a position sensitive electron detector 212 is arranged at a second position above the intermediate magnetic lens 213. Above the detector 212, the first lens system (not shown) is arranged, which is for example the same as the multi electron beam generator 2 as shown in FIG. 1, which focuses the primary electron beams 23 into a first array of separated spots in an intermediate plane where a position sensitive backscatter charged particle detector 212 is arranged, as shown in FIG. 2. The intermediate magnetic lens 213 is at least part of the second lens system for directing the primary electron beams 23 from the detector 212 plane towards the surface of the sample 215, and for focusing all primary charged particle beams 23 into a second array of individual spots. The second lens system comprises an electromagnetic lens which is common for the primary electron beams 23. One or more of the intermediate magnetic lens 213 and the objective lens 214 comprises the electromagnetic lens, which is arranged for rotating the array of primary electron beams 23 around the optical axis 28 to position the second array on the target 215 with respect to the first array at the detector 212 plane at an angle larger than 0 degrees and smaller than 180 degrees around the optical axis 8, as will be explained in more detail in the discussion of FIGS. 4 and 5 below.

Figure 3:
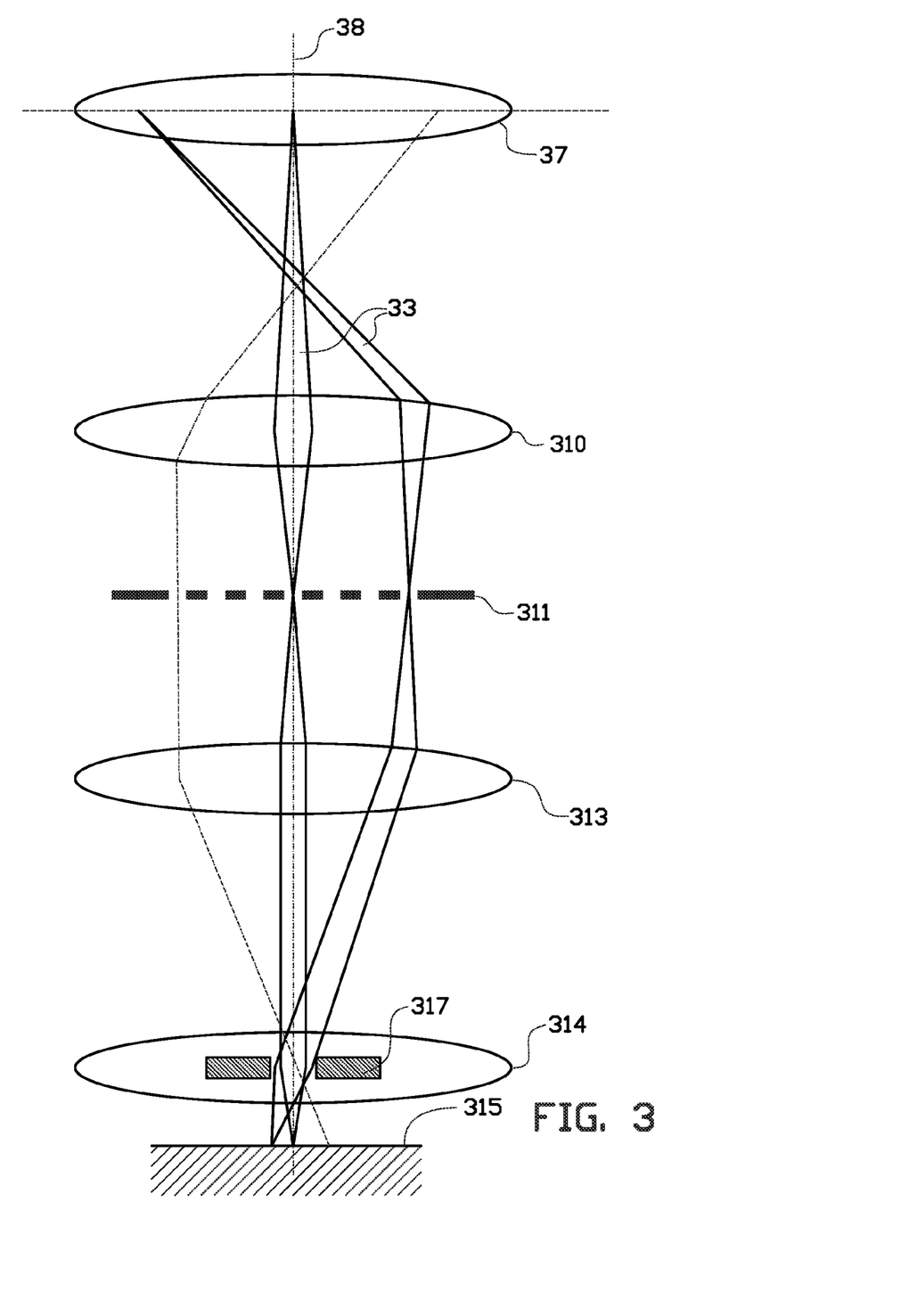
FIG. 3 shows part of the beam path of a third example of a MBSEM according to the invention.

FIG. 3 shows a further example of an optical setup in a MBSEM for detecting backscattered electrons. In this setup, the position sensitive backscatter electron detector 311 is arranged between a collimating lens 310 and a focusing lens 313. The accelerator lens 37 and the collimating lens 310 are at least part of the first lens system which focuses the primary electron beams 33 into a first array of separated spots in an intermediate plane where a position sensitive backscatter electron detector 311 is arranged, as shown in FIG. 3. The focusing lens 313 and the objective lens 314 are at least part of the second lens system for directing the primary electron beams 33 from the detector 311 plane towards the surface of the sample 315, and for focusing all primary charged particle beams 33 into a second array of individual spots. One or more of the focusing lens 313 and the objective lens 314 comprises an electromagnetic lens which is common for the primary electron beams 33 and is arranged for rotating the array of primary electron beams 33 around the optical axis to position the second array on the target 315 with respect to the first array at the detector 311 plane at an angle larger than 0 degrees and smaller than 180 degrees around the optical axis 38, as will be explained in more detail in the discussion of FIGS. 4 and 5 below. In the objective lens 314, a variable aperture 317 is arranged as a backscatter beam limiting aperture between the sample 315 and the detector 311.

When the focusing lens 313 is used as the electromagnetic lens for rotating the array of primary electron beams 33 around the optical axis 38, than the objective lens 314 can also be an electrostatic lens. It is noted that an electrostatic lens does not provide a rotation of the electron beams around the optical axis 38.

Figure 4:
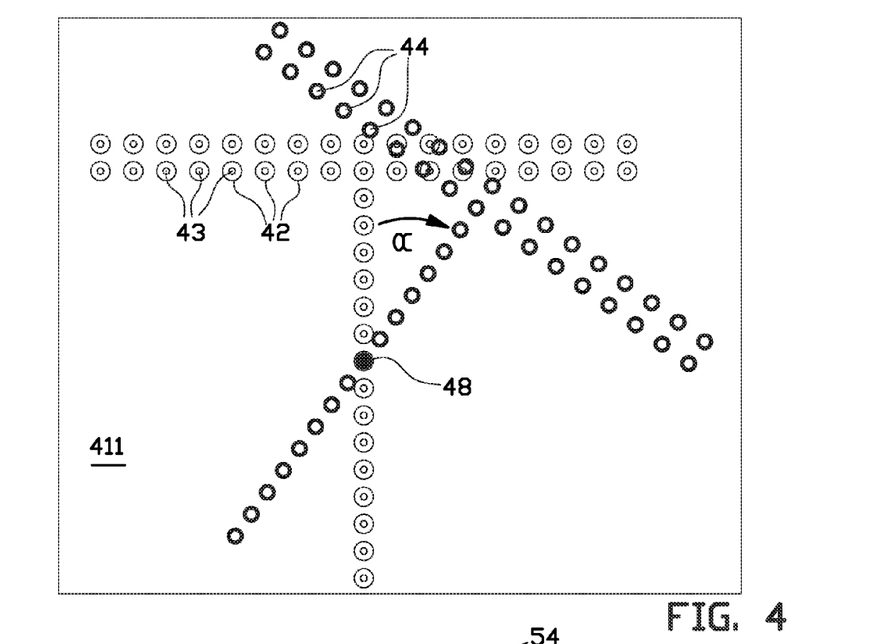
FIG. 4 shows a schematic cross section of the beam path of an example of a MBSEM according to the invention at the intermediate plane thereof.
Figure 5:
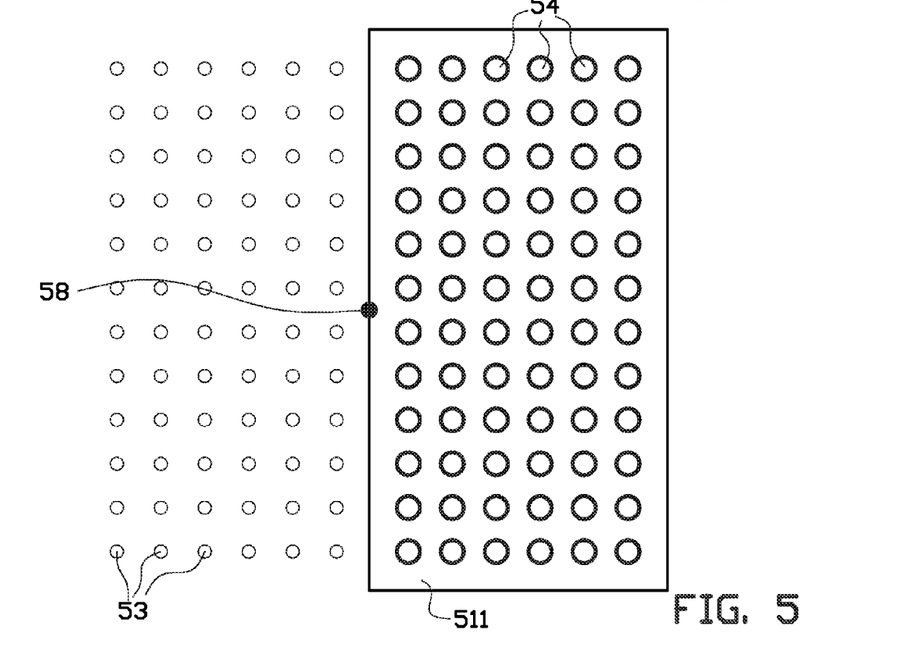
FIG. 5 shows a schematic cross section of the beam path of a further example of a MBSEM according to the invention at the intermediate plane thereof.

The effect of the rotation of electron beams 3, 13, 33 around the optical axis 8, 28, 38 is demonstrated in FIGS. 4 and 5.

FIG. 4 shows a schematic view of the surface of an example of a position sensitive backscatter electron detector 411, which surface faces the sample. The detector 411 is provided with an array of holes 42 for letting the primary charged particle beams 42 pass through on their way from the charged particle source 2 toward the sample surface 15. Since the detector 411 is arranged at least substantially in or near the intermediate plane where the charged particle beams 43 are focused, the detector 411 is arranged at a plane where the primary charged particle beams 43 are smallest. Thus the holes 42 in the detector 411 are sufficiently small to have enough surface area left for detecting the backscattered charged particles. The holes 42 are located at the position where the charged particle beams 43 are focused into the first array of separated spots.

Between the detector 411 and the sample an electromagnetic lens which is common for all charged particle beams and which is arranged for rotating the array of primary beams around the optical axis 48, the position of the second array of individual spots on the sample surface is rotated with respect to the holes 42 with an angle between 0 and 180 degrees. The backscattered charged particles, which also traverse the same electromagnetic lens, are also rotated with respect to the second array with substantially the same angle between 0 and 180 degrees. The array of spots 44 of the backscattered charged particles on the position sensitive detector 411 at the intermediate plane is thus rotated with respect to the primary charged particle beams 43 at an angle α larger than 0 degrees and smaller than 360 degrees around the optical axis 48. This rotation provides a spatial separation between the array of spots 44 of the backscattered charged particles with respect to the holes 42, which allows to arrange the array of spots 44 of the backscattered charged particles at a position in which they at least substantially deviate from the position of the primary beams 43. When the backscattered charged particles 44 impinge on the surface of the detector, they are converted into a signal which read out and this data is transferred to a computer for storage and/or further evaluation.

As shown in the example in FIG. 4, the plane where the primary beams 43 are smallest and where they traverse through the holes 42 is close to or arranged in the plane in which the backscattered charged particles are also focused into small spots 44.

The surface of the position sensitive detector 411 is covered by a large number of pixels and the spots 44 of backscattered charged particles on the detector 411 are detectable as long as one or more of the spots 44 do not overlie one or more of the holes 42. When using a position sensitive detector 411 with a large number of pixels, many more pixels than backscatter spots 44, it is not necessary to determine in advance where the backscatter spots 44 are going to end up exactly on the detector 411.

FIG. 5 shows a schematic view of the surface of a further example of a position sensitive backscatter electron detector 511, which surface faces the sample. This detector 511 is not provided with an array of holes. In stead, the detector 511 is arranged adjacent to the optical axis 58 and substantially covers half of the optical beam path of the charged particle optical system. The other half is without the obstruction of the detector 511 for letting the primary charged particle beams 53 pass through on their way from the charged particle source 2 toward the sample surface 15.

Again, an electromagnetic lens is arranged between the detector 511 and the sample, which lens is common for all charged particle beams and which is arranged for rotating the array of primary beams 53 around the optical axis 58. In this example the position of the second array of individual spots on the sample surface is rotated with respect to the primary beams 53 with an angle of approximately 90 degrees around the optical axis 58. The backscattered charged particles, which also traverse the same electromagnetic lens, are also rotated with respect to the second array in the same direction and with substantially the same angle of approximately 90 degrees. The array of spots 54 of the backscattered charged particles on the position sensitive detector 511 at the intermediate plane is thus rotated with respect to the primary charged particle beams 53 at an angle of approximately 180 degrees around the optical axis 58. Due to this rotation the array of spots 54 of the backscattered charged particles are moved to the side of the optical beam path where the detector 511 is positioned. When the backscattered charged particles 54 impinge on the surface of the detector 511, they are converted into a signal which read out and this data is transferred to a computer for storage and/or further evaluation.

In an embodiment, the position sensitive backscatter charged particle detector 411, 511 is a CCD camera, a CMOS camera, an array of avalanche photo diodes, photo multipliers or PN junction semiconductor detector which gets signal from backscatter charged particles directly. In an alternative embodiment the detector 411, 511 comprises a fluorescence screen at the intermediate plane, and an optical arrangement for conveying photons from the fluorescence screen onto a photon detector, such as a CCD camera, as described in more detail in the Dutch Patent Application 2009053, which is incorporated herein by reference.

Figure 6:
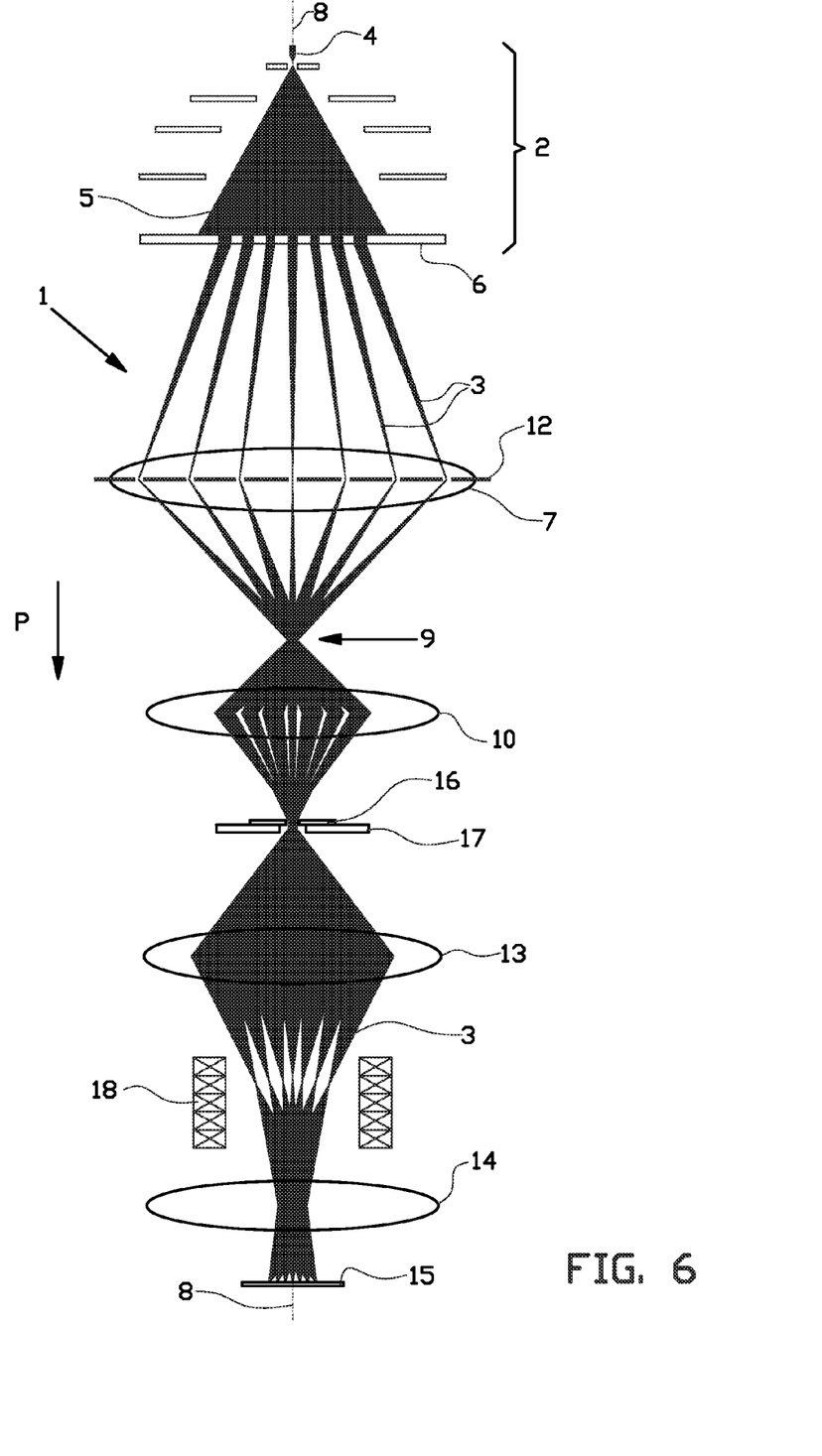
FIG. 6 shows an further example of a Multi-Beam Scanning Electron Microscope (MBSEM) according to the invention.

FIG. 6 shows essentially the same MBSEM as shown in FIG. 1 and as described in detail above, wherein the backscatter electron detector 12 in the position between the aperture lens array 6 and the magnetic condenser lens 10. The MBSEM as shown in FIG. 6 is furthermore provided with a position sensitive secondary electron detector 17 positioned at least substantially in or near a plane comprising a common cross-over, in this case directly below the variable aperture 16. This secondary electron detector 17 is arranged to acquire the individual secondary electron image of each single primary electron beam spot on the sample surface 15, and the backscatter electron detector 12 is arranged to acquire the individual backscatter electron image of each single primary electron beam spot on the sample surface 15. This means, that when the sample surface 15 is scanned in this MBSEM 1, multiple images of the backscattered electrons and the secondary electrons can be acquired at the same time in one single scan period.

In summary, the invention relates to an apparatus and method for inspecting a sample. The apparatus comprises a generator for generating an array of primary charged particle beams, and a charged particle optical system with an optical axis. The optical system comprises a first lens system for focusing all primary beams into a first array of spots in an intermediate plane, and a second lens system for focusing all primary beams into a second array of spots on the sample surface. The apparatus comprises a position sensitive backscattered charged particle detector positioned at or near the intermediate plane. The second lens system comprises an electromagnetic or electrostatic lens which is common for all charged particle beams. Preferably the second lens system comprises a magnetic lens for rotating the array of primary beams around the optical axis to position the second array with respect to the first array at an angle.

It is to be understood that the above description is included to illustrate the operation of the preferred embodiments and is not meant to limit the scope of the invention. From the above discussion, many variations will be apparent to one skilled in the art that would yet be encompassed by the spirit and scope of the present invention.

The invention claimed is:

1. An apparatus for inspecting a surface of a sample, wherein the apparatus comprises a multi beam charged particle generator for generating an array of primary charged particle beams, and a charged particle optical system with an optical axis comprising:
    a first lens system for focusing the primary charged particle beams into a first array of separated spots in an intermediate plane, and
    a second lens system for directing the primary charged particle beams from the intermediate plane towards the sample surface and which comprises an electromagnetic or electrostatic objective lens which is common for at least the primary charged particle beams for focusing all primary charged particle beams into a second array of individual spots on the sample surface,
    wherein the apparatus comprises a position sensitive backscatter charged particle detector positioned in or near the intermediate plane, wherein said detector comprises one or more through openings for passing said primary charged particle beams there through, and wherein said second lens system is arranged for projecting backscattered charged particles from the second array of individual spots on the sample surface into an array of backscattered charged particle spots on the detector.

2. Apparatus according to claim 1, wherein said one or more through openings comprises an array of holes wherein each hole of the array of holes is arranged for passing one of said array of primary charged particle beams there through.

3. Apparatus according to claim 2, wherein the diameter of the holes of the array of holes is substantially smaller than the pitch between the holes.

4. Apparatus according to claim 1, wherein the second lens system comprises one or more magnetic lenses which are arranged for rotating the array of primary charged particle beams around the optical axis on their way from said intermediate plane towards the sample, to position the second array with respect to the first array at an angle larger than 0 degrees and preferably smaller than 180 degrees around the optical axis.

5. Apparatus according to claim 4, wherein the one or more magnetic lenses are arranged for rotating the array of backscattered charged particle spots with respect to the first array at an angle larger than 0 degrees and preferably smaller than 360 degrees around the optical axis.

6. Apparatus according to claim 5, wherein the one or more magnetic lenses are arranged for rotating the array of backscattered charged particle spots with respect to the first array at an angle of substantially 180 degrees around the optical axis.

7. Apparatus according to claim 6, wherein the detector comprises one through opening for passing said primary charged particle beams there through.

8. Apparatus according to claim 1, wherein the second lens system is arranged for projecting the backscatter charged particles from the individual spots on the sample surface through a common cross-over of the backscattered charged particles to substantially individual spots on the position sensitive backscatter charged particle detector.

9. Apparatus according to claim 8, wherein an aperture is arranged in or near the plane comprising the common cross-over of the backscattered charged particles.

10. Apparatus according to claim 9, wherein said aperture comprises open areas to allow passage of certain angular directions of the backscattered charged particles, while blocking other angular directions.

11. Apparatus according to claim 1, wherein the position sensitive backscatter charged particle detector contains more than one pixel per backscatter charged particle beam.

12. Apparatus according to claim 1, wherein the position sensitive backscatter charged particle detector is a CCD camera, a CMOS camera, an array of avalanche photo diodes, photo multipliers or PN junction semiconductor detector which gets signal from backscatter charged particles directly.

13. Apparatus according to claim 1, wherein the position sensitive backscatter charged particle detector comprises a fluorescent screen arranged at least substantially in or near said intermediate plane and an optical arrangement for conveying photons from the fluorescent screen to a CCD camera, a CMOS camera, an array of avalanche photo diodes or photo multipliers.

14. Apparatus according to claim 13, wherein the CCD camera, CMOS camera, array of avalanche photo diodes or photo multipliers is positioned such that the array of detector pixels coincides with the array of images of the individual backscatter beams.

15. Apparatus according to claim 1, wherein the second lens system is arranged for imaging the first array of separated spots from said intermediate plane onto the sample surface with a magnification in a range from 0.01 to 0.2.

16. Apparatus according to claim 1, wherein the pitch between the spots in the second array of separated spots on the sample surface is between 0.3 and 30 micrometers.

17. Apparatus according to claim 1, wherein the second lens system is arranged for projecting the primary charged particle beams through a common cross-over, and wherein the apparatus comprises a position sensitive secondary electron detector positioned at least substantially in or near a plane comprising said common cross-over.

18. Apparatus according to claim 1, wherein the second lens system comprises magnetic and/or electrostatic charged particle deflectors for scanning the primary charged particle over the sample.

19. Apparatus according to claim 18, wherein the magnetic and/or electrostatic charged particle deflectors are arranged and/or controllable for obtaining a substantially stationary positioning of the array of backscattered charged particle spots on the detector during scanning.

20. Method for inspecting a surface of a sample comprising the steps of:
generating an array of primary charged particle beams using a multi beam charged particle generator;
focusing the primary charged particle beams into a first array of separated spots in an intermediate plane, using a first lens system;
directing the primary charged particle beams from the intermediate plane towards the sample surface using a second lens system and focusing all primary charged particle beams into a second array of individual spots on the sample surface using an electromagnetic or electrostatic objective lens which is common for at least the primary charged particle beams;
projecting backscattered charged particles from the second array of individual spots on the sample surface into an array of backscattered charged particle spots on the intermediate plane using said second lens system; and
detecting said backscattered charged particles using a position sensitive backscatter charged particle detector positioned in or near the intermediate plane, wherein said detector comprises one or more through openings for passing said primary charged particle beams there through.

21. Method according to claim 20, wherein the second lens system comprises one or more magnetic lenses which are arranged to rotate the array of primary charged particle beams around the optical axis on their way from said intermediate plane towards the sample, and to position the second array with respect to the first array at an angle larger than 0 degrees and preferably smaller than 180 degrees around the optical axis.

22. Method according to claim 21, wherein the one or more magnetic lenses are arranged to rotate the array of backscattered charged particle spots with respect to the first array at an angle larger than 0 degrees and preferably smaller than 360 degrees around the optical axis.

23. Method according to claim 22, wherein the one or more magnetic lenses are arranged to rotate the array of backscattered charged particle spots with respect to the first array at an angle of substantially 180 degrees around the optical axis.

24. Method according to claim 23, wherein the detector comprises one through opening for passing said primary charged particle beams there through.

25. Method according to claim 20, wherein the second lens system comprises magnetic and/or electrostatic charged particle deflectors to scan the primary charged particle over the sample.

26. Method according to claim 25, wherein the magnetic and/or electrostatic charged particle deflectors are arranged and/or controllable to obtain a substantially stationary positioning of the array of backscattered charged particle spots on the detector during scanning.

27. Method according to claim 25, in which the sample surface is moved at constant speed in a first direction while the primary charged particle beams are scanned repeatedly in a second direction at least substantially perpendicular to the first direction.

\* \* \* \* \*